United States Patent
Dargar et al.

(10) Patent No.: US 6,642,004 B2
(45) Date of Patent: Nov. 4, 2003

(54) METHOD FOR MEASURING NUCLEOTIDES

(75) Inventors: Ratna Dargar, Newtown, PA (US); Muniratham K. Chaguturu, West Windsor, NJ (US)

(73) Assignee: FMC Corporation, Philadelphia, PA (US)

( * ) Notice: Subject to any disclaimer, the term of this patent is extended or adjusted under 35 U.S.C. 154(b) by 13 days.

(21) Appl. No.: 10/040,517

(22) Filed: Nov. 7, 2001

(65) Prior Publication Data

US 2002/0142332 A1 Oct. 3, 2002

Related U.S. Application Data

(60) Provisional application No. 60/247,949, filed on Nov. 13, 2000.

(51) Int. Cl.[7] .............................. C12N 15/85; C07H 2/04
(52) U.S. Cl. ....................... 435/6; 536/23.5; 536/24.31; 435/4; 435/21; 435/963; 435/240.1; 435/320.1
(58) Field of Search .............................. 424/1.11; 435/4, 435/7.1, 7.2, 525, 252.3, 245.3, 69.1, 240.1; 436/518, 537, 501; 422/102; 536/23.5

(56) References Cited

U.S. PATENT DOCUMENTS 5,733,735 A    3/1998    Boime et al.

OTHER PUBLICATIONS

Kariv et al., "High Throughput Quantitation of camp Production Mediated by Activation of Seven Transmembrane Domain Receptors" Journal of Biomolecular Screening, vol. 1, No. 1, 1999 (pp. 27–32).*
Brown et al., A Simple and Sensitive Saturation Assay Method for the Measurement of Adenosine 3':5'–Cyclic Monophosphate Biochem J. (1971) 121, 561–562.*
Kariv et al in "High Throughput Quantitation of cAMP Production Mediated by Activation of Seven Transmembrane Domain Receptor" in Journal of Biomolecular Screening, vol. 1, No. 1, 1999 (pp. 27–32).*
A Rapid Filtration Assay for cAMP, Takeda et al., J. Biochem., 105, 327–329 (1989).
A Micro–Radioimmunoassay for the Measurement of Intracellular cAMP, Berg et al., BioTechniques, vol. 15, No. 1, 56–59 (1993).
A Simple and Sensitive Saturation Assay Method for the Measurement of Adenosine 3':5'–Cyclic Monophosphate, Brown et al., Biochem. J., 121, 561–562 (1971).
A Protein Binding Assay for Adenosine 3':5'–Cyclic Monophosphate, A. G. Gilman, Proc. N. A. S., vol. 67, No. 1, 305–312 (Sep. 1970).
Adenylate cyclase and cAMP, Farndale et al., Chapter 4 of Signal Transduction: A Practical Approach, IRL Press.
The Sf9 Cell Line as a Model for Studying Insect Octopamine–Receptors, Orr et al., Insect Biochem. Molec. Biol., vol. 22, No. 6, 591–597 (1992).
High Throughput Quantitation of cAMP Production Mediated by Activation of Seven Transmembrane Domain Receptors, Kariv et al., J. Biomolec. Screening, vol. 4, No. 1, 27–32 (1999).
Biotrak™ cAMP Direct Assay Advertisement, Amersham™ LIFESCIENCE (Sep. 1997).
International Search Report for PCT/US01/46345.
Competitive immunoassay (Cat–EIA), a helpful technique for catalytic antibody detection. Part I., Taran et al., Tetrahedron Letters 40 (1999) 1887–1890.
Enzyme Immunoassays of Adenosine Cyclic 3', 5'–Monophosphate and Guanosine Cyclic 3', 5'Monophosphate Using Acetylcholinesterase., Pradelles et al., Anal. Chem. 1989, 61, 447–453.
Biotrak cellular communications assays, camp enzymeimmunoassay (EIA) system, code RPN 225. Amersham Pharmacia Biotech., pp 1–63 (1999).
High Throughput Quantitation of cAMP Production Mediated by Activation of Seven Transmembrane Domain Receptors., Kariv et al., Journal of Biomolecular Screening.,4(1), pp. 27–32 (1999).
Assays for Drug Development and Research, Amersham Pharmacia Biotech, BioDirectory '99., pp. 11 (1999).
Product Information., Alexis Corporation., Http://guest:guest@www.alexis–corp.com/member/showprod.htm?prod=850–013 (Apr. 18, 2002) pp1–2.
New Products Since 1999/2000 Catalog, Alexis Corporation., Http://guest:guest@www.alexis–corp.com/member/showprod.htm?prod=850–013 (Apr. 18, 2002) pp. 1–33.

\* cited by examiner

Primary Examiner—Ethan Whisenant
Assistant Examiner—Shar Hashemi
(74) Attorney, Agent, or Firm—FMC Corporation

(57) ABSTRACT

The present invention discloses a one-pot, high-throughput method for the measurement of the amount of a nucleotide generated in a cell. The method is particularly effective in measuring changes in cyclic adenosine 3',5'-monophosphate (cAMP) coupled to cell receptors in insects.

25 Claims, No Drawings

METHOD FOR MEASURING NUCLEOTIDES

CROSS-REFERENCE TO RELATED APPLICATIONS

This application claims priority of U.S. Provisional Patent Application No. 60/247,949, filed Nov. 13, 2000.

FIELD OF THE INVENTION

The present invention relates generally to the field of nucleotides. In particular, the invention relates to measuring the potential biological activity of a compound by measuring nucleotide levels in cells following chemical treatment, and more particularly it pertains to measuring the levels of cyclic phosphate nucleotides present in cells following chemical treatment for measuring the potential biological activity of a compound.

BACKGROUND OF THE INVENTION

The physiological responses to many biologically active compounds are mediated through "second messengers". Nucleotides, for example cyclic adenosine 3',5'-monophosphate or cyclic AMP (cAMP), play important roles as second messengers in signal transduction pathways after hormones or other biologically active compounds bind to cell surface receptors. Increased levels of nucleotides, resulting from receptor activation, cause activation of specific nucleotide-dependent protein kinases, which in turn cause phosphorylation of various target proteins. It is the activation of these phosphorylated target proteins that bring about the diverse physiological responses in the cells including, but not limited to, biological activity. Thus, the higher the level of the nucleotide present the more biological activity a compound may possess.

The measuring of intracellular nucleotide levels following chemical treatment of cells has been reported in the literature, for example Takeda et al., J. Biochem., Vol. 105, pp. 327–329 (1989), Berg et al., Biotechniques, Vol. 15, No. 1, pp. 56–59 (1993), Brown et al., Biochem. J. 121, pp. 561–562 (1971), and A. G. Gilman, PNAS, Vol. 67, No. 1, pp. 305–312 (1970). However, these methods tend to involve multiple reaction vessels and be time-intensive limiting the number of measurements that can be carried out in a given time period. As such, these methods preclude a single vessel, i.e. "one-pot", high-throughput method for measuring changes in nucleotides. In addition, "one-pot" methods reported in the literature, for example Amersham LifeScience's commercially available Biotrak™ product and Kariv et al., J. Biomolecular Screening, Vol. 4, No. 1, pp. 27–32, (1999), tend to be expensive. As a result, there is a need for an inexpensive, single vessel, high-throughput method for measuring changes in the amount of a nucleotide present in a cell.

SUMMARY OF THE INVENTION

One embodiment of the present invention describes a single vessel, high-throughput method for measuring levels of nucleotides generated in a testing medium. The present invention measures changes in the amount of a nucleotide in a test medium in response to the addition of a test compound to the test medium. The present invention is particularly effective in measuring changes in a nucleotide, such as cyclic adenosine 3',5'-monophosphate (cAMP), in a cell, particularly in cells of insects.

In another embodiment of the present invention, a single vessel, high-throughput method of identifying compounds that which increase the amount of a nucleotide generated by a testing medium by comparing test compounds to the test medium alone or to the test medium following chemical treatment with compounds that increase nucleotides is disclosed. This method can be useful in identify compounds suspected of exhibiting biological activity.

In yet another embodiment of the present invention, a single vessel, high-throughput method of identifying compounds with biological activity through the generation of cAMP in a cell is disclosed.

The present invention is less complex, more cost effective, and comparable in sensitivity to those disclosed in the art.

DEFINITIONS

The modifier "about" as utilized herein indicates that certain preferred operating ranges, such as ranges for molar ratios for reactants, material amounts, and temperature, are not fixedly determined. The meaning will often be apparent to one of ordinary skill in the art of molecular biology. For example, a recitation of a temperature range of about 120° C. to about 135° C. in reference to an experiment would be interpreted to include other like temperatures that can be expected to favor a useful completion of the experiment, such as 105° C. or 150° C. In general, unless more particular ranges are disclosed, "about" shall indicate not more than 10% of the absolute value of an end point or 10% of the range recited, whichever is less.

The term "ambient temperature" as utilized herein shall mean any suitable temperature found in a laboratory or other working quarter, and is generally not below about 15° C. nor above about 30° C.

The term "biological activity" as utilized herein shall mean the ability of a substance, such as a chemical, including but not limited to drugs (i.e. pharmaceuticals) and pesticides, to act on a cell, virus, organ or organism and which creates a change in the functioning of the cell, virus, organ or organism.

The term "testing vessel" as utilized herein shall mean any device, such as a petri-dish, a microtiter plate, a test-tube, or beaker, which may be utilized to perform an assay, a reaction, a method, an experiment, or other procedure.

The term "testing medium" as used herein shall mean any environment, such as a cell or a cellular membrane, suitable for generating a nucleotide.

The term "nucleotide binding protein" as utilized herein shall mean any protein, for example, a protein derived from a bovine adrenal gland, a protein derived from a bovine muscle, or an antibody, that selectively binds or attaches to a nucleotide.

As used herein, the term "lysing agent" shall mean any substance, such as a detergent, capable of causing cell lysis.

DETAILED DESCRIPTION OF THE INVENTION

One embodiment of the present invention involves a method of measuring levels of a nucleotide generated in a testing medium, for example, cells or cellular membranes, following chemical treatment. The method comprises:

(a) contacting a test compound with the testing medium in a testing vessel, for example, a microtiter plate, a test-tube, or beaker;

(b) maintaining the test compound in contact with the testing medium in the testing vessel for a time sufficient to allow nucleotides to be generated in the testing medium;

(c) releasing nucleotides: generated in the testing medium into the testing vessel;

(d) adding a radiolabeled nucleotide ligand and a fixed amount of a nucleotide binding protein to the testing vessel, wherein the radiolabeled nucleotide ligand competes with nucleotides generated in the testing medium to bind to the nucleotide binding protein;

(e) maintaining the testing vessel for a period of time at a temperature sufficient to allow nucleotides generated in the testing medium and the radiolabeled nucleotide ligand to bind to the nucleotide binding protein to form a nucleotide binding protein complex;

(f) separating the nucleotide binding protein complex from uncomplexed radiolabeled nucleotide ligand; and (g) measuring the level of radioactivity of the nucleotide binding protein complex, wherein the level of radioactivity is inversely proportional to the amount of the nucleotide generated in said testing medium.

Suitable nucleotides that may be generated and measured by the present invention include, but are not limited to, cyclic phosphates. Preferable nucleotides generated and measured by the present invention are cyclic monophosphates, for example, cyclic adenosine 3',5'-monophosphate (cAMP), dibutyryl cyclic adenosine 3',5'-monophosphate (dbcAMP), cyclic guanosine 3',5'-monophosphate (cGMP), cyclic inosine 3',5'-monophosphate (cIMP), and cyclic uridine 3',5'-monophosphate(cUMP). Particularly preferred and useful nucleotides generated and measured by the present invention are cAMP and cGMP.

Suitable cells that may be used as the test medium in the present invention include, but are not limited to, native or cloned invertebrate or vertebrate cells which are either adherent or nonadherent, for example Sf9 cells, Sf21 cells, KC cells, CHO cells, COS7 cells, and HEK293 cells.

The test compound may be contacted neat or as a solution in a solvent. As used herein the term "neat" refers to the unmixed or straight technical material along with any impurities contained therein. Examples of solvents which may be used in the present invention are saline solutions, for example potassium, sodium, or magnesium saline solutions, a tissue culture media, buffers, for example acidic, basic, or neutral buffers, water, an acid, a ketone, an alcohol, a sulfoxide, or mixtures thereof. Preferably test compound is added as a solution in a tissue culture media, N,N-dimethylsulfoxide, methanol, acetone, or mixtures thereof. The test medium can also be added neat or as a solution in a solvent. The solvents set forth above may also be used in connection with the test medium.

The time sufficient to allow nucleotides to be generated in the testing medium is preferably from about five to 180, more preferably about five to about sixty, minutes, at about 15° C. to about 40° C., more preferably about 20° C. to about 40° C.

The nucleotides generated in the testing medium may be released into the testing vessel by methods known to one skilled in the art. Preferably, the nucleotide can be released into the testing vessel by lysing the test medium, for example, through the addition of a lysing agent, either neat or as a solution in the above disclosed solvents; mechanically disrupting the cell wall, for example, using ultrasound; freeze-thawing; heating; or acid and alkaline treatment; and then maintaining the testing medium at about 15° C. to about 40° C., preferably about 20° C. to about 40° C., for about 5 to about sixty, preferably for about 5 to about thirty, minutes. Preferably the testing medium is lysed through the addition of a lysing agent, such as a nonionic detergent, enzyme, or surfactant.

Preferably, the radiolabeled nucleotide ligand is a radiolabeled cyclic phosphate, more preferably, a radiolabeled cyclic monophosphate. Examples of radiolabeled nucleotide ligands that may be used include, but are not limited to, radiolabeled cyclic adenosine 3',5'-monophosphate, radiolabeled cyclic guanosine 3',5'-monophosphate, radiolabeled cyclic inosine 3',5'-monophosphate, or radiolabeled cyclic uridine 3',5'-monophosphate. Preferred radiolabeled nucleotide ligands that may be used in the present invention are radiolabeled cyclic adenosine 3',5'-monophosphate and radiolabeled cyclic guanosine 3',5'-monophosphate, more preferably radiolabeled cyclic adenosine 3',5'-monophosphate.

As set forth above, examples of nucleotide binding proteins that may be useful in the present invention are proteins derived from a bovine adrenal gland and muscle and antibodies. A preferred nucleotide binding protein that can be used in the present invention is a protein derived from a bovine adrenal gland. The time required for the nucleotides generated in the testing medium and the radiolabeled nucleotide ligand to bind to the nucleotide binding protein to form a nucleotide binding protein complex is not critical to the present invention. In general, maintaining the testing vessel at about 15° C. to about 40° C., preferably about 20° C. to about 40° C., for about 15 to about 120, preferably about 90 to about 120, minutes, is sufficient to allow nucleotides generated in the testing medium and the radiolabeled nucleotide ligand to bind to the nucleotide binding protein to form a nucleotide binding protein complex.

The nucleotide binding protein complex can be separated from the uncomplexed radiolabeled nucleotide ligand by methods known to one skilled in the art, such as filtration, centrifugation, solvent extraction or combinations thereof. Similarly, the level of radioactivity of the nucleotide binding protein complex, which is inversely proportional to the amount of the nucleotide generated, can be measured by methods known to one skilled in the art, such as scintillation counting or spectrophotometric methods (see, for example, A. G. Gilman, PNAS, Vol. 67, No. 1, pp. 305–312 (1970) incorporated herein by reference to the extent it discusses measuring the radioactivity of a complex the inverse relationship between the level of radioactivity and the amount of the nucleotide generated in a cell).

In another embodiment of the present invention, a method of identifying a compound that increases the amount of a nucleotide generated by a testing medium is disclosed. The method comprises performing a trial utilizing the method disclosed above and then comparing the results form the trial to results produced from either:

(a) a negative control in which no compound is contacted with the testing medium;

(b) appositive control using a positive control compound as the test compound, wherein the positive control compound is a compound that increases the amount of the nucleotide generated in a cell; or (c) both a positive control and a negative control; wherein an amount of nucleotide generated in the testing medium is greater than the nucleotide that appears in the testing medium in the negative control and an amount of nucleotide generated in the testing medium is greater than or equal to the amount of nucleotide generated in the testing medium in the positive control is indicative of a test compound which can increase the amount of nucleotide generated in a testing medium.

Preferably, the results from the trial are compared to results produced from both a positive control and a negative control; wherein an amount of nucleotide generated in the testing medium is greater than the nucleotide that appears in the testing medium and an amount of nucleotide generated in the testing medium is greater than or equal to the amount of nucleotide generated in the testing medium in the positive control is indicative of a test compound which can increase the amount of nucleotide generated in a testing medium.

Examples of positive control compounds that can be used in the present invention are octopamine, synephrine, demethylchlordimeform, or amitraz.

The method is particularly useful identifying compounds that exhibit biological activity. The testing mediums, nucleotides, testing vessels, radiolabeled nucleotide ligands, and nucleotide binding proteins including, but not limited to, the preferred testing mediums, nucleotides, testing vessels, radiolabeled nucleotide ligands; and nucleotide binding proteins disclosed above can also be used in this embodiment.

As set forth above, the time sufficient to allow nucleotides to be generated in the testing medium is about five to 180, preferably about five to sixty, minutes at about 15° C. to about 40° C., preferably about 20° C. to about 40° C.

Similarly, the nucleotides generated in the generated in the testing medium can be released into the testing vessel by the methods disclosed above, which are incorporated herein as if set forth at length.

As set forth above, maintaining the testing vessel at about 15° C. to about 40° C., preferably about 20° C. to about 40° C., for about 15 to about 120,preferably about 90 to about 120, minutes, is usually sufficient to allow nucleotides generated in the testing medium and the radiolabeled nucleotide ligand to bind to the nucleotide binding protein to form a nucleotide binding protein complex. The methods of separating the binding protein complex from uncomplexed radiolabeled nucleotide ligand and measuring level of radioactivity of the nucleotide binding protein complex set forth above can also be used in this embodiment.

In another embodiment of the present invention, a method of identifying a compound with biological activity is disclosed. The method comprises:

i) performing a trail comprising the steps of:
(a) contacting a test compound with a cell in a microtiter plate;
(b) maintaining the test compound in contact with the cell in the microtiter plate for a time sufficient to allow cyclic adenosine 3',5'-monophosphate to be generated in the cell;
(c) releasing cyclic adenosine 3',5'-monophosphate generated in the cell into the microtiter plate;
(d) adding radiolabeled cyclic adenosine 3',5'-mohophosphate and a fixed amount of a protein derived from a bovine adrenal gland to the microtiter plate, wherein the radiolabeled cyclic adenosine 3',5'-monophosphate competes with cyclic adenosine 3',5'-monophosphate generated in the cell to bind to the protein derived from a bovine adrenal gland;
(e) maintaining the microtiter plate at a temperature for a period of time sufficient to allow cyclic adenosine 3',5'-monophosphate generated in the testing medium and the radiolabeled cyclic adenosine 3',5'-monophosphate to bind to the protein derived from a bovine adrenal gland to form a cyclic adenosine 3',5'-monophosphate binding protein complex;
(f) separating the cyclic adenosine 3',5'-monophosphate binding protein complex from uncomplexed radiolabeled cyclic adenosine 3',5'-monophosphate; and
(g) measuring the level of radioactivity of the cyclic adenosine 3',5'-monophosphate, binding protein complex, wherein the level of radioactivity is inversely proportional to the amount of the cyclic adenosine 3',5'-monophosphate generated in said cell; and ii) comparing the results from the trial to results produced from either:
(a) a negative control in which no compound is contacted with the cell;
(b) a positive control using a positive control compound as the test compound, wherein the positive control compound is a compound that increases the amount of the cyclic adenosine 3',5'-monophosphate generated in a cell; or
(c) both a positive and a negative control; wherein an amount of cyclic adenosine 3',5'-monophosphate generated in the testing medium is greater than the cyclic adenosine 3',5'-monophosphate that appears in the cell in the negative control and an amount of cyclic adenosine 3',5'-monophosphate generated in the cell is greater than o equal to the amount of cyclic adenosine 3',5'-monophosphate generated in the cell in the positive control is indicative of a test compound which can increase the amount of cyclic adenosine 3',5'-monophosphate generated in a cell.

The positive control compounds disclosed above can also be used in this embodiment. Preferably, the positive control compound is octopamine or amitraz.

Preferably, the time sufficient to allow cyclic adenosine 3',5'-monophosphate to be generated in the cell is about five to 180, more preferably about five to about sixty, minutes at about 15° C. to about 40° C., more preferably about 20° C. to about 40° C. Preferably, the cyclic adenosine 3',5'-monophosphate generated in the cell is released into the microtiter plate by lysing, preferably through the addition of a lysing agent, such as a nonionic detergent, and maintaining the cell at about 15° C. to about 40° C., more preferably about 20° C. to about 40° C., for about 5 to about sixty, more preferably about 5 to about thirty, minutes.

Generally, the microtiter plate can be maintained for about 15 to about 120, preferably about 90 to about 120, minutes at about 15° C. to about 40° C., preferably about 20° C. to about 40° C., to allow cyclic adenosine 3',5'-monophosphate generated in the cell and the radiolabeled cyclic adenosine 3',5'-monophosphate to bind to the protein derived from a bovine adrenal gland to form the cyclic adenosine 3',5'-monophosphate binding protein complex. Once the cyclic adenosine 3',5'-monophosphate binding protein complex is formed it can be separated form the uncomplexed radiolabeled cyclic adenosine 3',5'-monophosphate and its radioactivity measured by the methods disclosed above. Preferably, the cyclic adenosine 3',5'-monophosphate binding protein complex is separated from the uncomplexed radiolabeled cyclic adenosine 3',5'-monophosphate by filtration and its radioactivity is measured by scintillation counting.

The present invention provides an improvement over other methods disclosed in the art in that it is a single vessel, high-throughput method for measuring increases in the amount of a nucleotide generated as well as a means of identifying compounds with biological activity which is less complex, more cost effective, yet comparable in sensitivity to those disclosed in the art.

The present invention is now described in more detail by reference to the following examples, but it should be understood that the invention is not construed as be limited thereto.

EXAMPLE 1

This example illustrates the quantification of cAMP generated from amitraz using t-octylphenoxypolyethoxyethanol as the lysing agent.

The following solutions were prepared on the same day the experiment was to be carried out:

Solution A: To about 450 ml of stirred deionized water was added 6.05 grams of tris(hydroxymethyl) aminomethane (TRIS (base), available from J.T. Baker Incorporated, Phillipsburg, N.J.), 3.4 ml of concentrated hydrochloric acid (available from J.T. Baker Incorporated), 7.3 grams of sodium chloride, 1.86 grams of ethylene diamine tetraacetic acid disodium salt (EDTA, available from Sigma Chemical Company, St. Louis, Mo.), 42.8 grams of sucrose (available from J.T. Baker Incorporated) and 0.5 ml of 2-mercaptoethanol (available from Sigma Chemical Company). The resulting solution was stirred and the pH adjusted to 7.4 with concentrated hydrochloric acid. Once at pH 7.4, sufficient deionized water was added to bring the total volume to 500 ml.

Solution B: To about 900 ml of deionized water was added 12.1 grams of tris(hydroxymethyl) aminomethane, 6.5 ml concentrated hydrochloric acid, 1.86 grams of EDTA, 1.44 grams of theophylline (available from Sigma Chemical Company), and 1 ml of 2-mercaptoethanol. The resulting solution was stirred for about five minutes and the pH adjusted to 7.4 with concentrated hydrochloric acid. Once at the appropriated pH, sufficient deionized water was added to bring the total volume to 1 liter.

Solution C1: 26.8 grams of sodium phosphate, dibasic, 7-hydrate (available from J.T. Baker Incorporated) was taken up in one liter of deionized water.

Solution C2: 13.8 grams of sodium phosphate, monobasic, monohydrate (available from J.T. Baker Incorporated);was taken up in one liter of deionized water.

Solution D: To about 500 ml of deionized water was added 81 ml of Solution C1 and 19 ml of Solution C2. The resulting solution was stirred for about five minutes and sufficient water was added to bring the total volume to one liter. Upon completion of addition, the pH was adjusted to 7.4 if necessary.

Solution E: To 880 ml of Solution D was added 120 ml of a 50% aqueous polyethyleneimine solution (available from Sigma Chemical Company).

Solution F1: To about 3.5 liters of deionized water was added 48.44 grams of tris(hydroxymethyl) aminomethane and 26 ml of concentrated hydrochloric acid. The resulting solution was stirred and additional hydrochloric acid was added until the pH was 7.4. Once at the appropriate pH; sufficient deionized water was added to bring the total volume to four liters.

Solution F2: To 100 ml of Solution F1 was added 900 ml of deionized water.

Solution G: To about 800 ml of deionized water was added 100 ml of solution F1 followed by 50 ml of Solution E. Upon completion of addition, sufficient deionized water was added to bring the total volume to 1000 ml.

Solution H: One gram (Triton® X -100, Sigma Ultra, t-octylphenoxypolyoxyethanol, available from Sigma Chemical Company) was taken up in Solution B to a total volume of 100 ml.

Solution J: 111 milligrams of 3-isobutyl-methylxanthine (IBMX, available from Sigma Chemical Company) was taken up in 10 ml of methanol.

Solution K: 4.1 milligrams of Forskolin (available from Sigma Chemical Company) was taken up in 10 ml of N,N-dimethylsulfoxide (DMSO, available from J.T. Baker Incorporated).

Solution M: 1.2 milligrams of cAMP (available from Sigma Chemical Company) was taken up in 10 ml of DMSO.

Solution O: To 10 ml of stirred, serum free Sf9 medium (Sf900 II SFM—GIBCO BRL Life Science Technologies, Grand Island, N.Y.) was added 0.02 ml of Solution J and 0.01 ml of Solution K. Upon completion of addition, the resulting solution was gently mixed until homogeneous.

Solution P (Binding Protein Solution): To a 1000 ml beaker was added 50 grams of thawed bovine adrenal glands (available from Pelfreeze Biologicals, Rogers, Ark.) followed by 500 ml of Solution A. The resulting solution was homogenized at O to 4° C. for two minutes in 30-second intervals. After this time, the solution was filtered, and the filtrate centrifuged in a High-Speed RC5B/C centrifuge (available from Sorvall, Newton, Conn.) at 16,000 rpm. The resulting supernatant was filtered through microcloth and stored in aliquots at −80° C. in a Revco™ deep freezer (available from Revco Scientific Inc. Asheville, N.C.) for later use.

Solution Q: To 10 ml of Solution P was added 10 ml of Solution B.

Solution R: To 10 ml of Solution B was added 0.02 ml of radiolabeled cyclic adenosine 3',5'-monophosphate stock solution ([$^3$H]cAMP stock, Cat. No.: TRK 559, available from Amersham Pharmacia Biotech, Piscataway, N.J.).

Solution S: One gram of (octylphenoxy) polyethoxyethanol (Igepal CA -630, available from Sigma Chemical Company) was taken up in about 100 ml of Solution B.

On the day of the experiment, four-day sold Sf9 cells for use in the first step, with cell density at about 5,000,000 to about 6,000,000 cells, were spun in a Biofuge 15 centrifuge (available from Heneaus Instruments, Germany at 1310 rpm (500 g) for five minutes. After this time, the supernatant was discarded and sufficient Sf9 serum free medium (Sf900 II SFM) was added to the resulting cell pellet give a final concentration of 2,000,000 cells /ml. To these cells was added 0.02 ml of Solution J. Upon completion of addition, the resulting solution was gently mixed and then incubated at ambient temperature for 40 minutes, for use, below .

In carrying out the first step, to each well of a 96 well microplate was added 100 μl of Solution O. Upon completion of addition, 5 μl of DMSO was added to the wells designated as control wells; 5 μl of various dilutions, ranging in concentration from about 0.00123 mM to about 0.03 mM, of amitraz (available from ChemService, West Chester, Pa.) in DMSO were added to the wells designated for binding; and 5 μl of Solution M was added to the wells designated for non-specific binding. Thereafter, 50 μl of the above-prepared Sf9 cell solution was added to all of the wells. The microplates were incubated at ambient temperature for 45 minutes. After this time, the Sf9 cells were lysed by adding 50 μl of Solution H. The microplates were incubated a second time at ambient temperature for 15 to 20 minutes. After this time, 25 μl of Solution R followed by 25 μl of Solution Q were added to the microplates. The microplates were incubated for a third time at ambient temperature with shaking at 125 rpm for 90 minutes. The resulting mixtures were filtered under reduced pressure through glass fiber filtermats, which were soaked in 500 ml of Solution G for about 30 minutes prior to use. The filtermats were washed for ten seconds with ice-cold Solution F and then, dried at 60° C. for 45 to 60 minutes in a Stabil-Therm® oven (available from Blue M Electric Co., Blue Island, Ill.). After this time, the amount of the radiolabeled 3',5'-monophosphate/binding protein complex bound to the filtermats was determined by the aforesaid quantification method. See Table 1 for results.

EXAMPLE 2

This example illustrates the quantification of cAMP generated from synephrine using t-octylphenoxypolyethoxyethanol as the lysing agent.

This method was performed in the manner disclosed in Example 1 except that synephrine was used rather than amitraz, and the concentrations of the synephrine dilutions were in the range of 0.00369 mM to 1.0 mM rather than 0.00123 mM to 0.3 mM. See Table 1 for results.

EXAMPLE 3

This example illustrates the quantification of cAMP generated from DL-octopamine using t-octylphenoxypolyethfoxyethanol as the lysing agent.

This method was performed in the manner disclosed in Example 1 except that DL-octopamine was used rather than amitraz, and the concentrations of the DL-octopamine dilutions were in the range of about 0.0123 mM to about 3.0 mM rather than about 0.00123 mM to about 0.3 mM. See Table 1 for results.

EXAMPLE 4

This example illustrates the quantification of cAMP generated from demethylchlordimeform (DCDM) using t-octylphenoxypolyethoxyethanol as the lysing agent.

This method was performed in the manner disclosed in Example 1 except that DCDM was used rather than amitraz, and the concentrations of the DCDM dilutions were in the range of 0.000123 mM to about 0.03 mM rather than 0.00123 mM to about 0.3 mM. See Table 1 for results.

EXAMPLE 5

This example illustrates the quantification of cAMP generated from demethylchlordimeform (DCDM) using (octylphenoxy)polyethoxyethanol as the lysing agent.

On the same day the experiment is to be carried, Solutions A–S are prepared again in the manner described above.

On the day of the experiment, four-day old Sf9 cells for use in the first step, about 5,000,000 to about 6,000,000, are spun in a Biofuge 15 centrifuge at 1310 rpm (500 g) for five minutes. After this time, the supernatant is discarded and sufficient Sf9 serum free medium (Sf900 II SFM) is added to the resulting cell pellet to give a final concentration of 2,000,000 cells/ml. To these cells is added 0.02 ml of Solution J. Upon completion of addition, the resulting solution is gently mixed and then incubated at ambient temperature for 40 minutes, for use below.

In the first step of this example, to each well of a 96 well microplate is added 100 μl of Solution O. Upon completion of addition, 5 μl of DMSO is added to the wells designated as control wells; 5 μl of various dilutions, ranging in concentration from 0.000123 mM to about 0.03 mM, of DCDM in methanol are added to the cells designated for binding; and 5 μl of Solution M is added to the wells designated for non-specific binding. Thereafter, 50 μl of the above-prepared Sf9 cell solution is added to all of the wells. The microplates are incubated at ambient temperature for 45 minutes. After this time, the Sf9 cells are lysed by adding 50 μl of Solution H. The microplates are incubated a second time at ambient temperature for 15 to 20 minutes. After this time, 25 μl of Solution R followed by 25 μl of Solution Q are added to the microplates. The microplates are incubated for a third time at ambient temperature with shaking at 125 rpm for 90 minutes. The resulting mixtures are filtered under reduced pressure through glass fiber filtermats, which are soaked in 500 ml of Solution G for about 30 minutes prior to use. The filtermats are washed for ten seconds with ice-cold Solution F and then dried at 60° C. for 45 to 60 minutes in a Stabil-Therm® oven.

As the results of Table 1 indicate, the present invention determined that all of the test compounds generated enough cAMP as to inhibit the binding of the radio-labeled cAMP to the available cell receptors even at low levels of concentration (see, for example, DCDM had 11.7% inhibition at the 0.0000041 millmolar (mM) concentration level) where as the controls did not generate any cAMP at all. Thus, it will be seen that the present invention can be useful. in predicting whether or not a prospective bioactive agent is likely to exhibit biological activity because as set forth above the higher the level of a nucleotide present the more biological activity a compound may possess.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

The present invention describes an improved method for measuring increases in nucleotides generated by testing medium as well as an improved method for determining biological activity. Said method is an improvement over those disclosed in the art in that it is a single vessel, high-throughput method that is less expensive, more cost effective and comparable in sensitivity to those disclosed in the art.

TABLE 1

Biocidal Activity of Bioactive Agents

| Compound | Total Concentration (millimolar (mM)) | Total Counts (dpm) Determined | Specific Counts[3] (dpm) | % Inhibition[4] |
|---|---|---|---|---|
| Control[1] | — | 7163.7 | 6771.2 | 0 |
| cAMP | 0.0000026 | 5791 | 5398.5 | 20.3 |
| Standard | 0.0000078 | 4627.3 | 4234.8 | 37.5 |
|  | 0.000023 | 2988.3 | 2595.8 | 61.7 |
|  | 0.00007 | 1828.3 | 1435.8 | 78.8 |
|  | 0.00021 | 1041.3 | 648.8 | 90.4 |
|  | 0.00064 | 700.3 | 307.6 | 95.5 |
| Non-specific[2] | — | 392.5 | — | — |
| Control[1] | — | 7340.2 | 6383.4 | 0 |
| DL-octopamine | 0.00041 | 6899 | 5942.2 | 6.9 |
|  | 0.00123 | 6595.9 | 5639.1 | 11.7 |
|  | 0.0037 | 5909.2 | 4952.4 | 22.4 |
|  | 0.0111 | 4252.3 | 3295.5 | 48.4 |
|  | 0.0333 | 2891.1 | 1934.3 | 69.7 |
|  | 0.1 | 2224.7 | 1267.9 | 80.1 |
| Non-specific[2] | — | 956.8 | — | — |
| Control[1] | — | 7245.4 | 6274.6 | 0 |
| Synephrine | 0.000123 | 7052.5 | 6081.7 | 3.1 |
|  | 0.00037 | 6230.8 | 5260 | 16.2 |
|  | 0.000111 | 5487 | 4516.2 | 28 |
|  | 0.00333 | 3703.5 | 2732.7 | 56.4 |
|  | 0.011 | 2575.9 | 1605.1 | 74.4 |
|  | 0.033 | 2045.4 | 1074.6 | 82.9 |

TABLE 1-continued

Biocidal Activity of Bioactive Agents

| Compound | Total Concentration (millimolar (mM)) | Total Counts (dpm) Determined | Specific Counts[3] (dpm) | % Inhibition[4] |
|---|---|---|---|---|
| Non-specific[2] | — | 970.8 | — | — |
| Control[1] | — | 7053 | 6174 | 0 |
| Amitraz | 0.000041 | 6899.4 | 6020.4 | 2.5 |
|  | 0.000123 | 6009.2 | 5130.2 | 16.9 |
|  | 0.00037 | 4818.2 | 3939.2 | 36.2 |
|  | 0.00111 | 3441.5 | 2562.5 | 58.5 |
|  | 0.00333 | 2307.2 | 1428.2 | 76.9 |
|  | 0.01 | 1928.5 | 1049.5 | 83 |
| Non-specific[2] | — | 879 | — | — |
| Control[1] | — | 7268.7 | 6444.4 | 0 |
| DCDM | 0.0000041 | 6512.1 | 5687.8 | 11.7 |
|  | 0.0000123 | 5779.0 | 4954.7 | 23.1 |
|  | 0.000037 | 4818 | 3993.7 | 38 |
|  | 0.000111 | 3513.7 | 2689.4 | 58.3 |
|  | 0.000333 | 2297.1 | 1472.8 | 77.1 |
|  | 0.001 | 1850.5 | 1026.2 | 84.1 |
| Non-specific[2] | — | 824.3 | — | — |

Notes:
[1]DMSO control.
[2]Cold or non-radiolabeled cAMP
[3]Specific Counts = Total Counts (dpm) Determined for Compound − Total Counts (dpm) Determined for Non-specific For example, the Specific Counts for a 0.1 mM solution of DL-octopamine would be 2224.7 − 956.8 = 1267.9.
[4]% Inhibition refers to the ability of the generated or unlabeled cAMP to inhibit the radio-labeled cAMP from binding to the available cell receptors, i.e. the amount of generated cAMP bound to the available cell receptors, and is calculated as follows: % Inhibition = [1 − (Specific Counts (dpm) of Compound ÷ Specific Counts (dpm) of Control)] × 100 For example, the % Inhibition for a 0.1 mM solution of DL-octopamine would be [1 − (1267.9/6383.4)] × 100 = 80.1%.

What is claimed:

1. A method for measuring levels of a nucleotide generated in a testing medium following chemical treatment, the method comprising:
   (a) contacting a test compound with the testing medium in a testing vessel;
   (b) maintaining the test compound in contact with the testing medium in the testing vessel for a time sufficient to allow nucleotides to be generated in the testing medium;
   (c) releasing nucleotides generated in the testing medium into the testing vessel;
   (d) adding a radiolabeled nucleotide ligand and a fixed amount of a nucleotide binding protein to the testing vessel, wherein the radiolabeled nucleotide ligand competes with nucleotides generated in the testing medium to bind to the nucleotide binding protein;
   (e) maintaining the testing vessel for a period of time at a temperature sufficient to allow nucleotides generated in the testing medium and the radiolabeled nucleotide ligand to bind to the nucleotide binding protein to form a nucleotide binding protein complex;
   (f) separating the nucleotide binding protein complex from uncomplexed radiolabeled nucleotide ligand; and
   (g) measuring the level of radioactivity of the nucleotide binding protein complex, wherein the level of radioactivity is inversely proportional to the amount of the nucleotide generated in said testing medium.

2. The method of claim 1, wherein the testing medium is a cell or cellular membrane.

3. The method of claim 1, wherein the nucleotide generated in the testing medium is a cyclic phosphate.

4. The method of claim 3, wherein the cyclic phosphate is a cyclic monophosphate.

5. The method of claim 1, wherein the time sufficient to allow nucleotides to be generated in the testing medium is about five to 180 minutes at about 15° C. to about 40° C.

6. The method of claim 1, wherein releasing nucleotides generated in the testing medium into the testing vessel comprises lysing and maintaining the testing medium at about 15° C. to about 40° C. for about 5 to about sixty minutes.

7. The method of claim 1, wherein the radiolabeled nucleotide ligand is a radiolabeled cyclic phosphate.

8. The method of claim 1, wherein the testing vessel is maintained at about 15° C. to about 40° C. for about 15 to about 120 minutes to allow nucleotides generated in the testing medium and the radiolabeled nucleotide ligand to bind to the nucleotide binding protein to form a nucleotide binding protein complex.

9. A method of identifying a compound which increases the amount of a nucleotide generated by a testing medium, the method comprising:
   i) performing a trial comprising the steps of:
      (a) contacting a test compound with the testing medium in a testing vessel;
      (b) maintaining the test compound in contact with the testing medium in the testing vessel for a time sufficient to allow nucleotides to be generated in the testing medium;
      (c) releasing nucleotides generated in the testing medium into the testing vessel;
      (d) adding a radiolabeled nucleotide ligand and a fixed amount of a nucleotide binding protein to the testing vessel, wherein the radiolabeled nucleotide ligand competes with nucleotides generated in the testing medium to bind to the nucleotide binding protein;
      (e) maintaining the testing vessel at a temperature for a period of time sufficient to allow nucleotides generated in the testing medium and the radiolabeled nucleotide ligand to bind to the nucleotide binding protein to form a nucleotide binding protein complex;
      (f) separating the nucleotide binding protein complex from uncomplexed radiolabeled nucleotide ligand; and
      (g) measuring the level of radioactivity of the nucleotide binding protein complex, wherein the level of radioactivity is inversely proportional to the amount of the nucleotide generated in said testing medium; and
   ii) comparing the results from the trial to results produced from either:
      (a) a negative control in which no compound is contacted with the testing medium;
      (b) a positive control using a positive control compound as the test compound, wherein the positive control compound is a compound that increases the amount of the nucleotide generated in the testing medium; or
      (c) both a positive control and a negative control; wherein an amount of nucleotide generated in the testing medium is greater than the nucleotide that appears in the testing medium in the negative control and an amount of nucleotide generated in the testing medium is greater than or equal to the amount of nucleotide generated in the testing medium in the positive control is indicative of a test compound which can increase the amount of nucleotide generated in the a testing medium.

10. The method of claim 9, wherein said method is used to identify a compound that exhibits biological activity.

11. The method of claim 9, wherein the testing medium is a cell or a cellular membrane.

12. The method of claim 9, wherein the nucleotide generated in the testing medium is a cyclic phosphate.

13. The method of claim 9, wherein the time sufficient to allow nucleotides to be generated in the testing medium is about five to 180 minutes at about 15° C. to about 40° C.

14. The method of claim 9, wherein releasing nucleotides generated in the testing medium into the testing vessel comprises lysing and maintaining the testing medium at about 15° C. to about 40° C. for about 5 to about sixty minutes.

15. The method of claim 9, wherein the radiolabeled nucleotide ligand is a radiolabeled cyclic phosphate.

16. The method of claim 9, wherein the testing vessel is maintained at about 15 to about 120 minutes at about 15° C. to about 40° C. to allow nucleotides generated in the testing medium and the radiolabeled nucleotide ligand to bind to the nucleotide binding protein to form a nucleotide binding protein complex.

17. A method of identifying a compound with biological activity, the method comprising:
   i) performing a trial comprising the steps of:
      (a) contacting a test compound with a cell in a microtiter plate;
      (b) maintaining the test compound in contact with the cell in the microtiter plate for a time sufficient to allow cyclic adenosine 3',5'-monophosphate to be generated in the cell;
      (c) releasing cyclic, adenosine 3',5'-monophosphate generated in the cell into the microtiter plate;
      (d) adding radiolabeled cyclic adenosine 3',5'-monophosphate and a fixed amount of a protein derived from a bovine adrenal gland to the microtiter plate, wherein the radiolabeled cyclic adenosine 3',5'-monophosphate competes with cyclic adenosine 3',5'-monophosphate generated in the cell to bind to the protein derived from a bovine adrenal gland;
      (e) maintaining the microtiter plate at a temperature for a period of time sufficient to allow cyclic adenosine 3',5'-monophosphate generated in the cell and the radiolabeled cyclic adenosine 3',5'-monophosphate to bind to the protein derived from a bovine adrenal gland to form a cyclic adenosine 3',5'-monophosphate binding protein complex;
      (f) separating the cyclic adenosine 3',5'-monophosphate binding protein complex from uncomplexed radiolabeled cyclic adenosine 3',5'-monophosphate; and
      (g) measuring the level of radioactivity of the cyclic adenosine 3',5'-monophosphate binding protein complex, wherein the level of radioactivity is inversely proportional to the amount of the cyclic adenosine 3',5'-monophosphate generated in said cell; and
   ii) comparing the results from the trial to results produced from either:
      (a) a negative control in which no compound is contacted with the cell;
      (b) a positive control using a positive control compound as the test compound, wherein the positive control compound is a compound that increases the amount of the cyclic adenosine 3',5'-monophosphate generated in a cell; or
      (c) both a positive and a negative control; wherein an amount of cyclic adenosine 3',5'-monophosphate generated in the cell is greater than the cyclic adenosine 3',5'-monophosphate that appears in the cell in the negative control and an amount of cyclic adenosine 3',5'-monophosphate generated in the cell is greater than or equal to the amount of cyclic adenosine 3',5'-monophosphate generated in the cell in the positive control is indicative of a test compound which can increase the amount of cyclic adenosine 3',5'-monophosphate generated in a cell.

18. The method of claim 17, wherein the time sufficient to allow cyclic adenosine 3',5'-monophosphate to be generated in the cell is about five to 180 minutes at about 15° C. to about 40° C.

19. The method of claim 17, wherein releasing cyclic adenosine 3',5'-monophosphate generated in the cell into the microtiter plate comprises lysing and maintaining the cell at about 15° C. to about 40° C. for about 5 to about sixty minutes; wherein the cell is lysed through the addition of a lysing agent.

20. The method of claim 17, wherein the microtiter plate is maintained at about 15 to about 120 minutes at about 15° C. to about 40° C. to allow cyclic adenosine 3',5'-monophosphate generated in the cell and the radiolabeled cyclic adenosine 3',5'-monophosphate to bind to the protein derived from a bovine adrenal gland to form the cyclic adenosine 3',5'-monophosphate binding protein complex.

21. The method of claim 2, wherein the cell or cellular membrane is a cell or cell membrane of an insect.

22. The method of claim 10, wherein the compound exhibits biocidal activity.

23. The method of claim 10, wherein the compound exhibits pesticidal activity.

24. The method of claim 17, wherein the compound exhibits biocidal activity.

25. The method of claim 17, wherein the compound exhibits pesticidal activity.

* * * * *